United States Patent
Tsuchiya et al.

(10) Patent No.: US 11,504,080 B2
(45) Date of Patent: Nov. 22, 2022

(54) X-RAY COMPUTED TOMOGRAPHY APPARATUS

(71) Applicant: Canon Medical Systems Corporation, Otawara (JP)

(72) Inventors: Nobuto Tsuchiya, Nasushiobara (JP); Tooru Kato, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 25 days.

(21) Appl. No.: 17/152,866

(22) Filed: Jan. 20, 2021

(65) Prior Publication Data
US 2021/0219930 A1 Jul. 22, 2021

(30) Foreign Application Priority Data
Jan. 21, 2020 (JP) .............................. JP2020-007440

(51) Int. Cl.
*A61B 6/00* (2006.01)
*A61B 6/03* (2006.01)

(52) U.S. Cl.
CPC ............ *A61B 6/4241* (2013.01); *A61B 6/032* (2013.01); *A61B 6/4488* (2013.01)

(58) Field of Classification Search
CPC ..... A61B 6/4241; A61B 6/032; A61B 6/4488; A61B 6/4035; A61B 6/4291; A61B 6/035
See application file for complete search history.

(56) References Cited

U.S. PATENT DOCUMENTS

| | | | |
|---|---|---|---|
| 2009/0154648 A1 | 6/2009 | Watanabe | |
| 2016/0007949 A1 | 1/2016 | Kobayashi et al. | |
| 2018/0292551 A1* | 10/2018 | Danielsson | ............... G01T 1/16 |
| 2018/0300909 A1 | 10/2018 | Tamura et al. | |

FOREIGN PATENT DOCUMENTS

| | | |
|---|---|---|
| JP | 2008-036399 A | 2/2008 |
| JP | 2008-053061 A | 3/2008 |
| JP | 2013-056119 A | 3/2013 |
| JP | 2016-027850 A | 2/2016 |
| JP | 2020-003450 A | 1/2020 |

* cited by examiner

*Primary Examiner* — Courtney D Thomas
(74) *Attorney, Agent, or Firm* — Oblon, McClelland, Maier & Neustadt, L.L.P.

(57) ABSTRACT

According to one embodiment, an X-ray computed tomography apparatus includes an X-ray tube, a photon counting detector, and processing circuitry. The X-ray tube radiates X-rays. The photon counting detector detects the X-rays radiated from the X-ray tube and transmitted through a subject. The processing circuitry adjusts a temperature adjustment amount used for regulating a temperature of the photon counting detector according to an imaging mode.

15 Claims, 8 Drawing Sheets

X-RAY COMPUTED TOMOGRAPHY APPARATUS

CROSS-REFERENCE TO RELATED APPLICATIONS

This application is based upon and claims the benefit of priority from prior Japanese Patent Application No. 2020-007440, filed Jan. 21, 2020, the entire contents of which are incorporated herein by reference.

FIELD

Embodiments described herein relate generally to an X-ray computed tomography apparatus.

BACKGROUND

X-ray computed tomography (CT) image quality depends on components or units within a gantry unit and is particularly influenced by the temperature of a detector, or a non-uniform temperature distribution (temperature non-uniformity) among detecting elements. To suppress such temperature non-uniformity, conventional X-ray CT apparatuses adopted a technique of adjusting the detector temperature using a fan-utilizing air cooling unit and a heater. However, the air cooling method does not permit fine control of the detector temperature as, for example, the volume of air fed from the fan varies due to rotations of the gantry unit, and as such, temperature non-uniformity may still occur in the detector.

Meanwhile, next-generation X-ray CT apparatuses that employ a photon counting detector (a photon counting CT apparatus, or a "PCCT apparatus") are expected to be used in the operations where a switchover between imaging modes including a substance discrimination mode and a substance non-discrimination mode, or a switchover between substance discrimination modes of different bin numbers, is often performed. In such operations, the amount of heat generated by the detector before the imaging mode switchover and that generated after the imaging mode switchover would differ greatly from each other. Especially for the next-generation X-ray CT apparatuses, therefore, adopting the conventional temperature adjusting technique can even increase the likelihood of temperature non-uniformity events in the detectors.

DETAILED DESCRIPTION

In general, according to one embodiment, an X-ray computed tomography apparatus includes an X-ray tube, a photon counting detector, and processing circuitry. The X-ray tube radiates X-rays. The photon counting detector detects the X-rays radiated from the X-ray tube and transmitted through a subject. The processing circuitry adjusts a temperature adjustment amount used for regulating a temperature of the photon counting detector according to an imaging mode.

The X-ray CT apparatus according to an embodiment will be described with reference to the drawings. The description will assume that components or portions having the same reference sign operate in the same manner, and redundant explanations will be omitted as appropriate.

Figure 1:
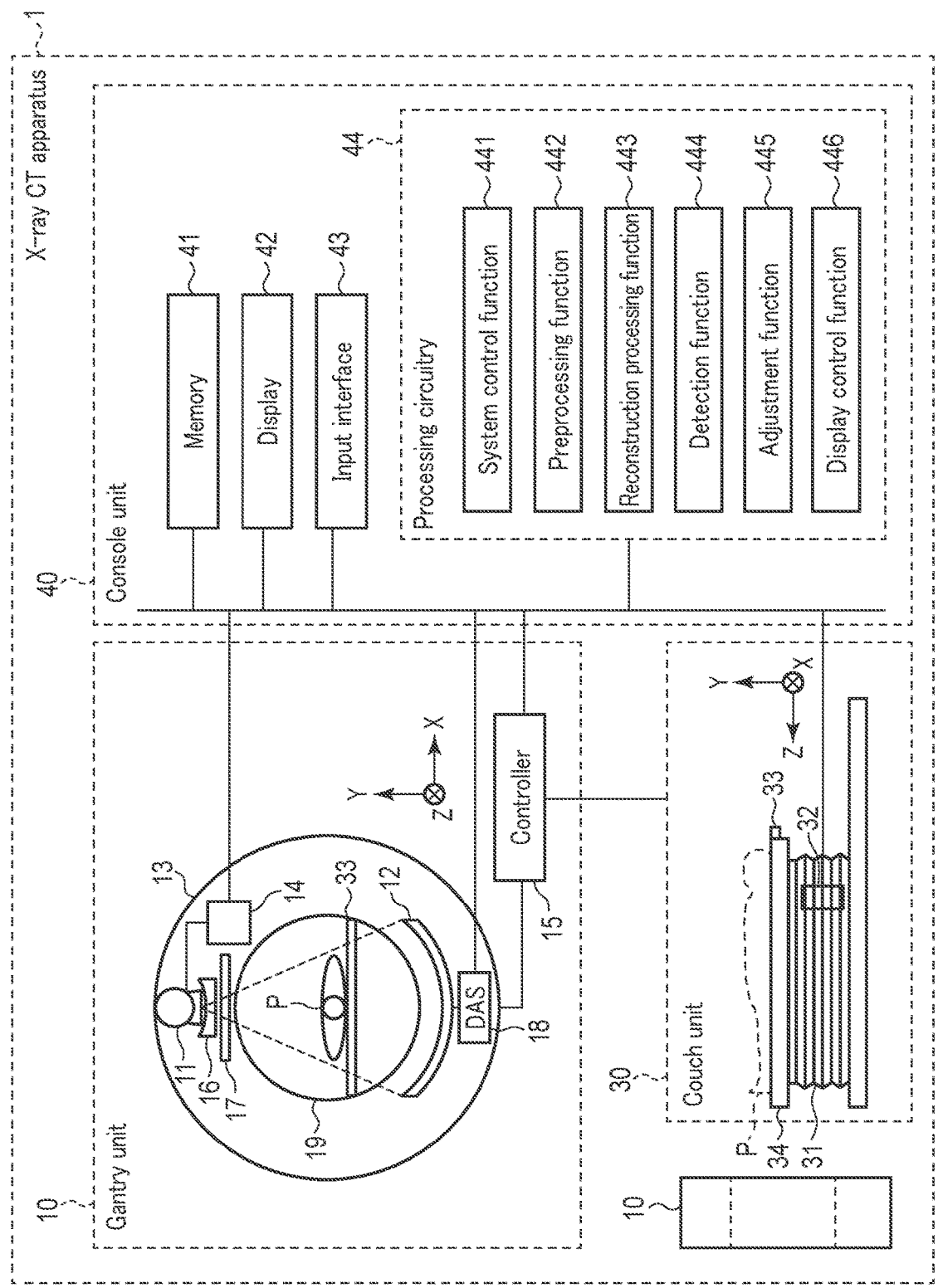
FIG. 1 is a diagram showing an exemplary configuration of an X-ray CT apparatus according to an embodiment.

FIG. 1 will be referred to for explaining an exemplary configuration of the X-ray CT apparatus according to the embodiment. The X-ray CT apparatus shown in FIG. 1, denoted by reference sign "1", includes a gantry unit 10, a couch unit 30, and a console unit 40. Note that, for describing the embodiment, the rotational-axis direction of a rotary frame 13 in its non-tilted state, or the longitudinal direction of a top 33 of the couch unit 30, is defined as a Z-axis direction. The axial direction orthogonal to the Z-axis direction and horizontal to the floor face is defined as an X-axis direction, and the axial direction orthogonal to the Z-axis direction and vertical to the floor face is defined as a Y-axis direction.

For example, the gantry unit 10 and the couch unit 30 are arranged in a CT examination room, and the console unit 40 is arranged in a control room that may be adjacent to the CT examination room. The console unit 40 does not have to be arranged in the control room. The console unit 40 may be arranged together with the gantry unit 10 and the couch unit 30 in the same room, for example. In any case, the gantry unit 10, the couch unit 30, and the console unit 40 are communicably connected to one another either via fixed lines or wirelessly.

Figure 2:
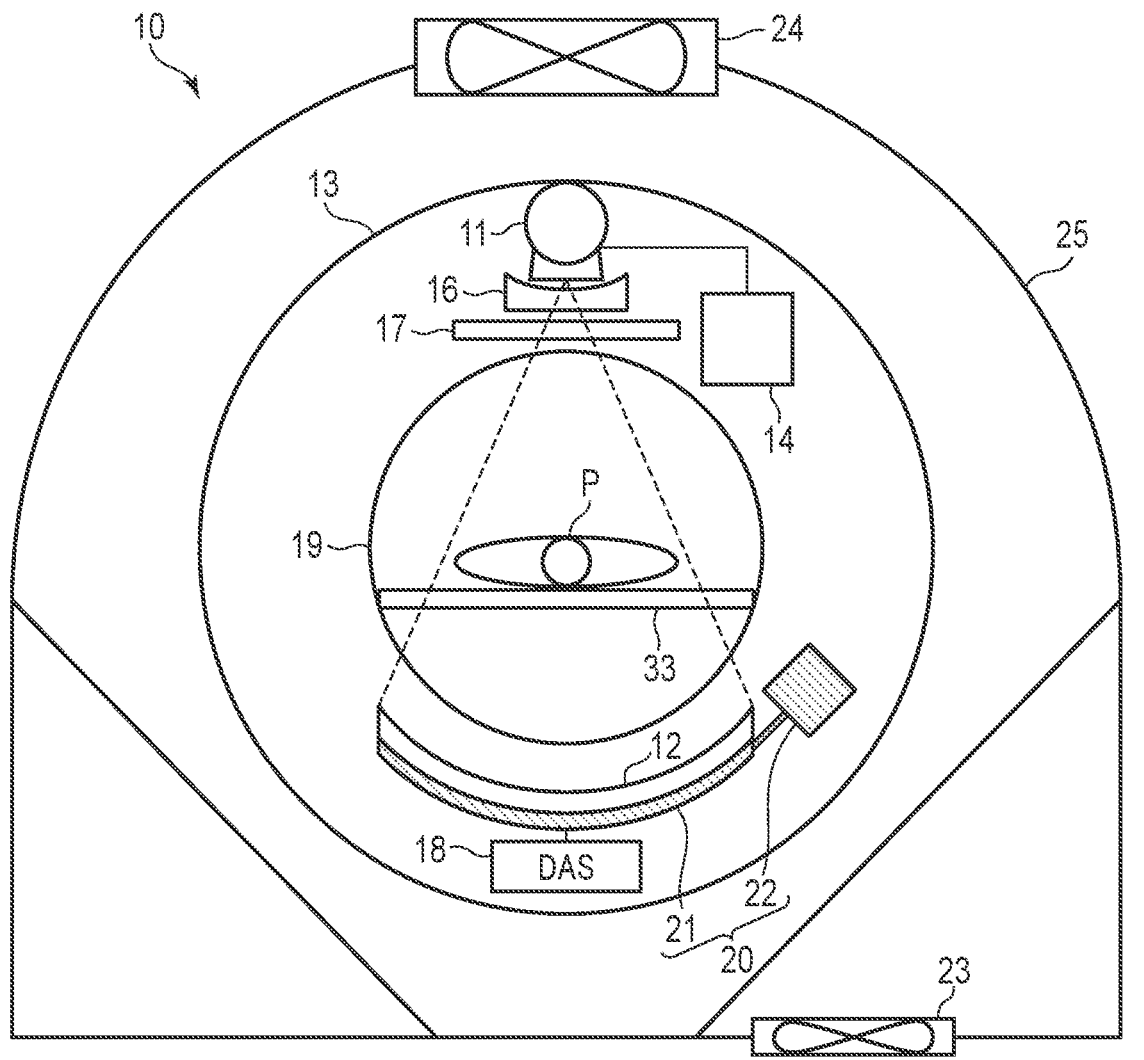
FIG. 2 is a diagram showing an exemplary configuration of a gantry unit according to the embodiment.

The gantry unit 10 is a scanner unit having a configuration to perform X-ray CT imaging for a subject P. The gantry unit 10 includes an X-ray tube 11, a detector 12, the rotary frame 13, an X-ray high-voltage device 14, a controller 15, a wedge 16, a collimator 17, and a data acquisition system (DAS) 18. For the sake of explanation, only some of the components are illustrated here. A more detailed configuration of the gantry unit 10 is shown in FIG. 2.

The X-ray tube 11 is a vacuum tube that generates X-rays by emitting thermal electrons from the cathode (filament) toward the anode (target) using a high-voltage application and a filament current supply from the X-ray high-voltage device 14. More specifically, the thermal electrons are caused to collide with the target to produce X-rays. Examples available as the X-ray tube 11 include a rotating anode-type X-ray tube that generates X-rays by emitting thermal electrons toward a rotating anode. The X-rays generated by the X-ray tube 11 are, for example, shaped into a cone beam through the collimator 17 and radiated toward the subject P. The X-ray tube 11 is one example of an X-ray generator.

The detector 12 detects the X-rays that have been radiated from the X-ray tube 11 and transmitted through the subject P, and outputs an electrical signal corresponding to the dose of the X-rays to the DAS 18. The detector 12 includes, for example, multiple rows of X-ray detecting elements such that the multiple X-ray detecting elements in each row are arranged in the channel direction and along a single arc that has its center coinciding with the focal point of the X-ray tube 11. For example, the detector 12 has an array structure in which such multiple rows, each with the X-ray detecting elements arranged in the channel direction, are disposed in the slice direction (row direction).

Figure 3:
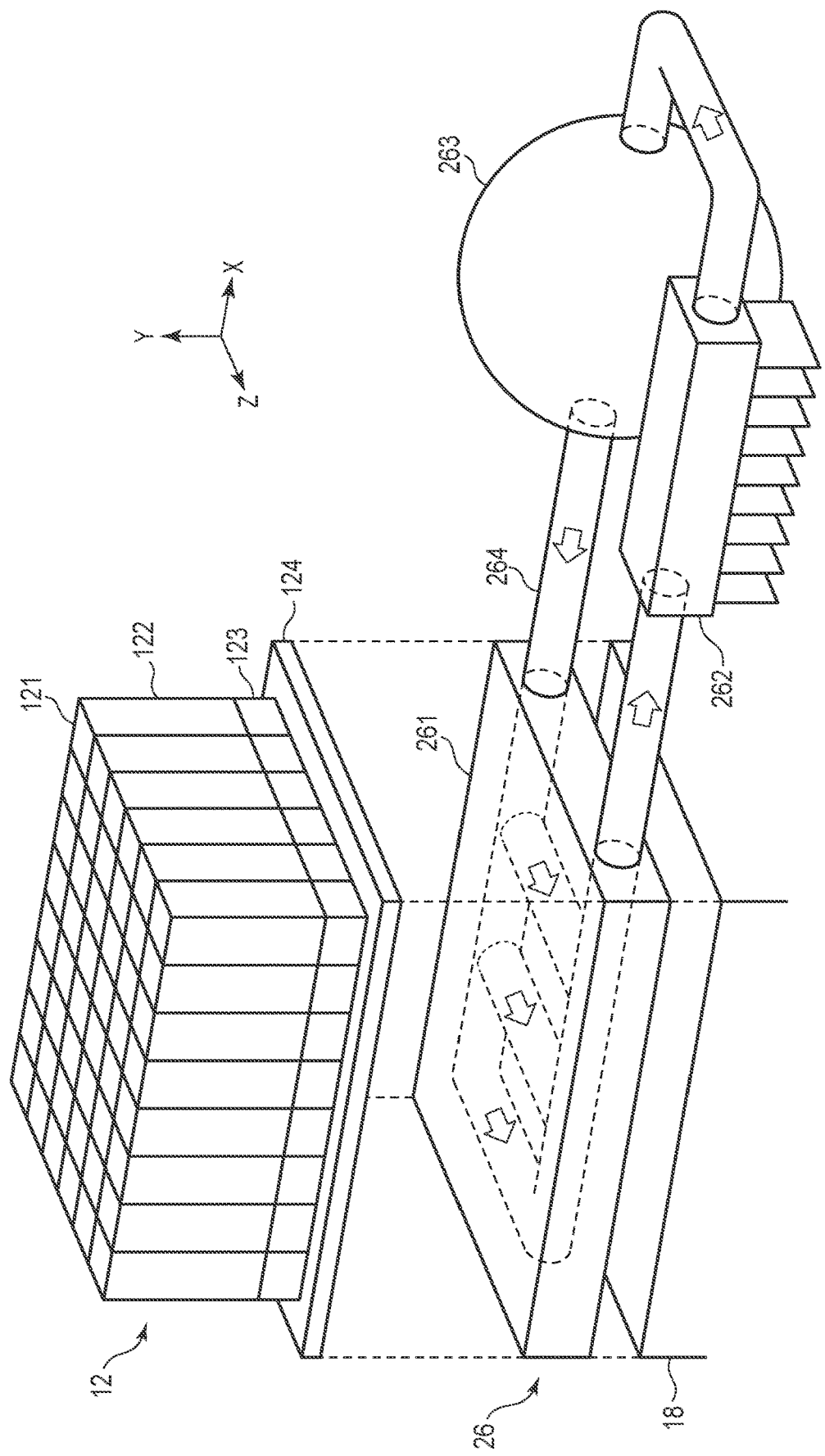
FIG. 3 is a diagram showing an exemplary configuration of a cooling unit according to the embodiment.

The detector 12 is, for example, an indirect conversion-type detector including a grid 121, a scintillator array 122, an optical sensor array 123, and a substrate 124. The indirect conversion-type detector converts incident X-rays into visible light using scintillators and then converts the visible light into electric signals. Note that the detector 12 may instead be a direct conversion-type detector including semiconductor elements for converting incident X-rays into electrical signals. The detector 12 is one example of an X-ray detector. The structure of the detector 12 is shown in FIG. 3.

Note that the detector 12 may be either an energy integrating detector or a photon counting detector, according to the measurement scheme adopted for the DAS 18 for measuring the electric signals obtained after the conversion. The detector 12 as an energy integrating detector integrates energy of the X-rays transmitted through the subject P for a predetermined period so that the sum of the transmitted X-ray energy corresponding to the predetermined period is measured. The detector 12 as a photon counting detector counts the number of X-ray photons included in the X-rays transmitted through the subject P, for each of multiple energy bands (which may be called "energy bins", or simply "bins"). This enables substance discrimination to be carried out based on imaging data acquired for each energy band. In the present disclosure, the imaging mode selected when substance discrimination is carried out is called a "substance discrimination mode", and the imaging mode selected when substance discrimination is not carried out is called a "substance non-discrimination mode". FIG. 1 assumes an exemplary instance where a photon counting detector is adopted as the detector 12.

The grid 121 is provided on the X-ray incident-side face of the scintillator array 122 and includes an X-ray shielding plate that has a function of absorbing scattered X-rays. The grid 121 may be called a collimator (one-dimensional collimator or two-dimensional collimator).

The scintillator array 122 includes multiple scintillator elements. Each scintillator element converts an incident X-ray into a given number of photons that corresponds to the intensity of the incident X-ray.

The optical sensor array 123 has a function of amplifying the light from the scintillator elements and converting the light into electrical signals so that output signals (energy signals) having wave height values according to the energy of the incident X-rays are produced. The optical sensor array 123 includes, for example, an optical sensor such as a photomultiplier tube (PMT).

The substrate 124 passes the output signals produced by the optical sensor array 123 on to the DAS 18.

The rotary frame 13 supports the X-ray generator and the X-ray detector in such a manner that they can rotate about the rotational axis Z. More specifically, the rotary frame 13 is a circular frame that supports the X-ray tube 11 and the detector 12 so that they face each other, and rotates them under the control of the controller 15. The rotary frame 13 is rotatably supported by a stationary frame (not illustrated) formed of metal, such as aluminum. To be more specific, the rotary frame 13 may be connected to the rim of the stationary frame via bearings. The rotary frame 13 receives power from a drive mechanism in the controller 15 to rotate about the rotational axis Z at a constant angular velocity.

The rotary frame 13 may further carry and support components such as the X-ray high-voltage device 14 and the DAS 18, in addition to the X-ray tube 11 and the detector 12. The rotary frame 13 of such a configuration is accommodated in a substantially cylindrical housing 25 having a bore 19 for forming an imaging space. The bore substantially conforms to a field of view (FOV). The bore has a center axis that coincides with the rotational axis Z of the rotary frame 13. While not illustrated, imaging data generated by the DAS 18 is transmitted in an optical communication manner from a transmitter that uses a light-emitting diode (LED) to a receiver that is located at the non-rotating portion (e.g., the stationary frame) of the gantry unit 10 and that uses a photodiode. The imaging data is then transferred to the console unit 40. Note that the manner of transmitting the imaging data from the rotary frame 13 to the non-rotating portion of the gantry unit 10 is not limited to such an optical communication, but any technique may be adopted as long as it permits contactless data transmissions.

The X-ray high-voltage device 14 includes a high-voltage generator and an X-ray controller. The high-voltage generator includes electric circuitry such as a transformer and a rectifier, and has a function of generating a high voltage to be applied to the X-ray tube 11 and a filament current to be supplied to the X-ray tube 11. The X-ray controller controls output voltages in accordance with the X-rays to be radiated by the X-ray tube 11. The high-voltage generator may adopt a transformer system or an inverter system. The X-ray high-voltage device 14 may be provided in the rotary frame 13 or at a part of the stationary frame of the gantry unit 10.

The controller 15 includes processing circuitry constituted by a central processing unit (CPU), etc., and the aforementioned drive mechanism constituted by a motor, an actuator, etc. The processing circuitry includes, as hardware resources, one or more processors such as a CPU as mentioned and a microprocessing unit (MPU), and one or more memories such as a read only memory (ROM) and a random access memory (RAM). The controller 15 may also be realized by any of an application specific integrated circuit (ASIC) and a field programmable gate array (FPGA), or other complex programmable logic device (CPLD) or simple programmable logic device (SPLD). The controller 15 controls the X-ray high-voltage device 14, the DAS 18, etc., according to commands given from the console unit 40. Each processor here reads programs stored in the memory or memories and executes them to realize the intended control.

The controller 15 further has a function of controlling operations of the gantry unit 10 and the couch unit 30 in response to input signals given from an input interface 43 furnished at the console unit 40 or the gantry unit 10. For example, the controller 15 controls rotations of the rotary frame 13, tilts of the gantry unit 10, and motions of the couch unit 30 and the top 33, upon receipt of the input signals. Here, the tilting control for the gantry unit 10 is realized by the controller 15 causing the rotary frame 13 to rotate about the axis that is parallel to the X-axis direction, based on tilt angle information input via the input interface 43 furnished at, for example, the gantry unit 10. The controller 15 may be provided in the gantry unit 10 or in the console unit 40. The controller 15 may be configured so that the programs are directly incorporated into the processor circuitry, instead of being stored in the memory. In this case, the processor reads the programs incorporated into its circuitry and executes them to realize the control.

The wedge 16 is a filter for adjusting the dose of X-rays radiated from the X-ray tube 11. More specifically, the wedge 16 is an attenuation filter which permits the X-rays radiated from the X-ray tube 11 to pass through itself so that the X-rays traveling toward the subject P will have a predetermined distribution. For example, the wedge 16 may be a wedge filter, a bow-tie filter, or the like, prepared by processing aluminum into a shape having a predetermined target angle and thickness.

The collimator 17 is constituted by lead strips, etc., and employed to narrow down the irradiation range of the X-rays that have passed through the wedge 16. The collimator 17 forms a slit using a combination of the multiple lead strips, etc. The collimator 17 may be called an X-ray diaphragm.

The DAS 18 generates, for each of multiple energy bands, digital data (which may be called "imaging data") indicative of a count value of the X-ray photons detected by the detector 12. The imaging data is a set of data including a channel number and a row number of the originating X-ray detecting element, a view number indicative of the acquired view (projection angle), and a count value with an identification by the energy bin number. The DAS 18 is realized by, for example, an application specific integrated circuit (ASIC) on which circuitry elements capable of generating the imaging data are mounted. The imaging data is transferred to the console unit 40.

The couch unit 30 is an apparatus unit on which the subject P is placed as a scan subject and that moves the subject P, and includes a base 31, a couch driver 32, the aforementioned top 33, and a support frame 34.

The base 31 is a housing that supports the support frame 34 in such a manner that the support frame 34 can move vertically.

The couch driver 32 is a motor or an actuator that moves the top 33, on which the subject P is placed, in the longitudinal direction of the top 33. The couch driver 32 moves the top 33 under the control of the console unit 40 or the controller 15. For example, the couch driver 32 moves the top 33 in a direction orthogonal to the subject P placed on the top 33 so that the body axis of the subject P coincides with the center axis of the bore of the rotary frame 13. The couch driver 32 may also move the top 33 along the body-axis direction of the subject P according to the X-ray CT imaging performed with the gantry unit 10. To generate force for movement, the couch driver 32 operates at a rotational rate corresponding to the duty ratio of the drive signals from the controller 15, etc. The couch driver 32 is realized by, for example, a motor such as a direct drive motor or a servo motor.

The top 33 is provided on the upper part of the support frame 34, and may be a plate for the subject P to lie on. Note that the couch driver 32 may move not only the top 33 but also the support frame 34 in the longitudinal direction of the top 33.

The console unit 40 includes a memory 41, a display 42, the aforementioned input interface 43, and processing circuitry 44. The memory 41, the display 42, the input interface 43, and the processing circuitry 44 perform data communications via a bus. Note that while the description assumes the console unit 40 to be a member separate from the gantry unit 10, the console unit 40 may be incorporated into the gantry unit 10, or part of its components may be included in the gantry unit 10.

The memory 41 is a storage device such as a hard disk drive (HDD), a solid state drive (SSD), or an integrated circuit storage device, that stores various information items. The memory 41 stores, for example, said imaging data and reconstructed image data. Other than an HDD, an SSD, or the like, the memory 41 may be a portable storage device such as a compact disc (CD), a digital versatile disc (DVD), or a flash memory, or a driver that reads and writes various information in cooperation with a semiconductor memory device, etc., including a random access memory (RAM). Also, the storage region of the memory 41 may be within the X-ray CT apparatus 1 or within an external storage device connected via a network. In an exemplary implementation, the memory 41 stores data of CT images, display images, etc. The memory 41 also stores control programs according to the embodiment.

The display 42 displays various information items. For example, the display 42 may output medical images (CT images) generated by the processing circuitry 44, graphical user interfaces (GUIs) for accepting various operations from an operator, and so on. The display 42 may discretionarily be, for example, a liquid crystal display (LCD), a cathode-ray tube (CRT) display, an organic electroluminescence display (OELD), a plasma display, or any other display available. The display 42 may be provided at the gantry unit 10. Also, the display 42 may be a desktop type, or implemented as a tablet terminal or the like that is capable of wireless communications with the main part of the console unit 40.

The input interface 43 receives various input operations from an operator and converts the received input operations into electrical signals for output to the processing circuitry 44. For example, the input interface 43 accepts acquisition conditions to apply when acquiring the imaging data, reconstruction conditions to apply when reconstructing CT images, image-processing conditions to apply when generating post-processed images from the CT images, and so on, from an operator. The input interface 43 may discretionarily be, for example, a mouse, a keyboard, a trackball, switches, buttons, a joystick, a touch pad, a touch-panel display, etc., or any combination thereof. Note that the embodiment does not limit the input interface 43 to a member with a physical operational component such as a mouse, a keyboard, a trackball, switches, buttons, a joystick, a touch pad, and a touch-panel display. That is, the examples of the input interface 43 also include processing circuitry for electric signals, which receives an electric signal corresponding to an input operation from a separate external input device, and outputs this electric signal to the processing circuitry 44. The input interface 43 may be provided at the gantry unit 10. The input interface 43 may instead be implemented as a tablet terminal or the like that is capable of wireless communications with the main part of the console unit 40.

The processing circuitry 44 takes total control over the X-ray CT apparatus 1 according to the electrical signals attributed to the input operations, which are output from the input interface 43. For example, the processing circuitry 44 includes, as hardware resources, one or more processors such as a CPU, an MPU, a graphics processing unit (GPU), etc., and one or more memories such as a ROM a RAM, etc. The processing circuitry 44, using the processor that runs the programs loaded into the memory, implements various functions including a system control function 441, a preprocessing function 442, a reconstruction processing function 443, a detection function 444, an adjustment function 445, and a display control function 446. It is not required that the functions (the system control function 441, the preprocessing function 442, the reconstruction processing function 443, the detection function 444, the adjustment function 445, the display control function 446, etc.) are realized by single processing circuitry. Multiple independent processors may be employed together to form processing circuitry so that the processors run the programs to realize the respective functions.

The system control function 441 controls each function of the processing circuitry 44 based on the input operations accepted from an operator via the input interface 43. More specifically, the system control function 441 reads the control program stored in the memory 41, loads it into the memory in the processing circuitry 44, and controls each component of the X-ray CT apparatus 1 according to the loaded control program.

The preprocessing function 442 performs preprocessing, such as logarithmic conversion, offset correction, interchannel sensitivity correction, and beam hardening correction, on the imaging data output from the DAS 18 to produce preprocessed, corrected imaging data.

The reconstruction processing function 443 generates CT image data by subjecting the corrected imaging data generated by the preprocessing function 442 to reconstruction processing that adopts a filtered back-projection (FBP) technique, an iterative approximation reconstruction technique, etc.

Here, the imaging data was generated based on the counting result obtained at the detector 12, so it contains information of the X-ray energy that was attenuated due to the transmission through the subject P. Accordingly, the reconstruction processing function 443 can reconstruct, for example, CT image data of specific energy components. The reconstruction processing function 443 may reconstruct CT image data for each of multiple energy components.

The detection function 444 detects imaging modes. The imaging mode here includes, for example, at least one of an imaging mode such as a substance discrimination mode, etc., and/or a bin number. The detection function 444 may detect an imaging condition including at least one of parameters for the tube current and tube voltage, and/or the imaging mode.

The adjustment function 445 adjusts a temperature adjustment amount used for regulating the temperature of the detector 12 according to the imaging mode. The temperature adjustment amount includes a cooling amount, which is how much the temperature of the detector 12 should be reduced, and a heating amount, which is how much the temperature of the detector 12 should be raised. For example, the adjustment function 445 adjusts the cooling amount by controlling one or more cooling units which may each be a liquid-cooling unit, an air-cooling unit, or an electron-cooling unit. The adjustment function 445 may adjust the temperature adjustment amount according to imaging conditions. The adjustment function 445 is one example of an adjuster.

The display control function 446 controls the display 42 to present information about the progress or results of ongoing or completed processes performed by each function of the processing circuitry 44, etc.

The processing circuitry 44 also performs scan control processing and image processing.

The scan control processing includes controlling various X-ray scan-related operations, such as causing the X-ray high-voltage device 14 to supply high voltages so that the X-ray tube 11 radiates X-rays.

The image processing includes converting the CT image data generated by the reconstruction processing function 443 into tomographic data of a given section, three-dimensional image data, etc., through the known technique based on the input operations accepted from an operator via the input interface 43.

It is not a limitation that the processing circuitry 44 is included in the console unit 40, but the processing circuitry 44 may be included in an integrated server provided for batch processing of data sets acquired at multiple medical image diagnostic apparatuses.

Also, while the description has assumed that the console unit 40 performs multiple functions as a single console, the console unit 40 may be constituted by multiple, separate consoles to perform the multiple functions. For example, functions of the processing circuitry 44 such as the preprocessing function 442 and the reconstruction processing function 443 may be distributed in different consoles.

Next, FIG. 2 will be referred to for explaining an exemplary configuration of the gantry unit 10 according to the embodiment. The figure shows a cooling unit 20, an air inlet 23, an air outlet 24, and the aforementioned housing 25, as well as the components of the gantry unit 10 shown also in FIG. 1. Among these, the cooling unit 20 is hatched.

The cooling unit 20 cools the detector 12. The cooling unit 20 includes a first heat exchanger 21 and a second heat exchanger 22. The cooling unit 20 is controlled by, for example, the adjustment function 445.

As a concrete configuration, the cooling unit 20 is movably supported by the rotary frame 13 together with the X-ray tube 11 and the detector 12. The cooling unit 20 is constituted such that the first heat exchanger 21 is in thermal contact with the detector 12 while extending in the channel direction of the detector 12, and the second heat exchanger 22 is disposed on the side of at least one lateral end of the detector 12. In one exemplary implementation, the first heat exchanger 21 is arranged immediately beneath the detector 12 in such a manner as to cover the entirety of the detector 12, that is, to contact at least the entire bottom face of the detector 12, and the second heat exchanger 22 is arranged on the side of one lateral end of the detector 12.

The cooling unit 20 also includes a connecting section physically connecting the first heat exchanger 21 and the second heat exchanger 22 with each other. In the cooling unit 20, a cooling medium for thermal exchange circulates among the first heat exchanger 21 and the second heat exchanger 22 via the connecting section. The connecting section may constitute a part of the first heat exchanger 21 or the second heat exchanger 22.

Here, the first heat exchanger 21 includes a cooling section and realizes cooling of the detector 12 by absorbing heat from the detector 12. The second heat exchanger 22 includes a heat dissipation section and realizes cooling of the detector 12 by discharging the heat that has been absorbed from the detector 12 by the first heat exchanger 21 to the outside of the cooling unit 20. To enable this mechanism, the housing 25 includes, at the position or positions near the heat dissipation section of the second heat exchanger 22, at least one air inlet 23 for taking air from the outside of the gantry unit 10 as a supply to the heat dissipation section, and at least one air outlet 24 for discharging air from the interior of the gantry unit 10.

The housing 25 may be designed to include such one or more air inlets 23 at any position as long as the air inlets 23 allow the air flowing from the outside of the gantry unit 10 to efficiently cool the heat dissipation section of the second heat exchanger 22 when the rotary member carrying the X-ray tube 11, the detector 12, and the cooling unit 20 is in a stationary, non-rotating state. The air inlets 23 may be arranged at, for example, the positions in the bottom face of the gantry unit 10 which are substantially below the heat dissipation section of the second heat exchanger 22.

The housing 25 may be designed to include said one or more air outlets 24 at any position as long as the air outlets 24 allow the air warmed up by the heat dissipation section of the second heat exchanger 22 to be efficiently discharged to the outside of the gantry unit 10 when the rotary member carrying the X-ray tube 11, the detector 12, and the cooling unit 20 is in a stationary, non-rotating state. The air outlets 24 may be arranged at, for example, the positions in the top face of the gantry unit 10 which are substantially above the heat dissipation section of the second heat exchanger 22.

The size, number, etc. of the air inlets 23 and the air outlets 24 may also be discretionarily changed. For realizing active air intake and discharge, the air inlets 23 and the air outlets 24 may be provided with a fan or fans. Each fan may, for example, be covered with a detachable cover component having a mesh structure. The fans may be controlled by the processing circuitry 44.

Next, FIG. 3 will be referred to for explaining an exemplary configuration of the cooling unit according to the embodiment. The description will assume the case of employing a liquid-cooling unit 26 as one example of the cooling unit 20. Also, for the sake of explanation, the figure shows the detector 12 and the liquid-cooling unit 26 vertically separate from each other so that their positional relationship is illustrated. In the actual configuration, the detector 12 and the liquid-cooling unit 26 are adjacent or closely in contact with each other to permit thermal exchange operations therebetween.

The liquid-cooling unit 26 cools the detector 12 with a liquid-form cooling medium, and includes a cold plate 261, a heat sink 262, a pump 263, and a conduit 264.

The cooling medium may be purified water, or a liquid mixture consisting of purified water and an additive such as ethylene glycol, etc. That is, any liquid may be employed as long as it allows for the thermal exchange.

The cold plate 261 is one example of the first heat exchanger 21 and it conducts the thermal exchange between the detector 12 and the liquid flowing in the cold plate 261. More concretely, the cold plate 261 is disposed between the substrate 124 of the detector 12 and the DAS 18. The cold plate 261 is arranged so that it does not block the signal line connections between the substrate 124 and the DAS 18. The cold plate 261 disposed in this manner can cool the detector 12 through the substrate 124.

Note that the DAS 18 also generates heat in proportion to the heat generation by the detector 12, and as such, the cold plate 261 disposed as above is expected to receive not only the heat from the detector 12 but also the heat from the DAS 18. Accordingly, a heat shield material may be provided between the cold plate 261 and the DAS 18, and/or the surface of the cold plate 261 that faces the DAS 18 may be formed from a material of high heat shielding properties, so that the detector 12 will be cooled first. Alternatively, or additionally, the cooling capacity of the cold plate 261 may be increased so that the detector 12 can be cooled even with the heat coming from the DAS 18. If a support plate for physically supporting the substrate 124 is used directly below the substrate 124, the cold plate 261 may be disposed directly below this support plate.

The cold plate 261 is a component including, for the liquid, an inlet, a flow path, and an outlet. The flow path in the cold plate 261 is one example of the cooling section of the first heat exchanger 21. The cold plate 261 may be formed of a material that gives a high thermal conduction efficiency, for example, one or more metal materials such as copper, aluminum, etc., as the cold plate 261 conducts the thermal exchange between the substrate 124 in contact with the surface of the cold plate 261 and the liquid flowing through the flow path. The cold plate 261 may have any shape as long as it matches the shapes of the substrate 124 and the DAS 18.

The flow path in the cold plate 261 may be freely designed, utilizing any straight, curved, meandering profiles, etc., so that the detector 12 can be cooled entirely and uniformly. The diameter, length, number, shape, etc. of the flow path may also be freely determined. The inlet and the outlet for the liquid may be provided at any position in the surface of the cold plate 261, which may be, for example, in the side surface of the cold plate 261 that is closest to the heat sink 262 and the pump 263 so that the most economical liquid circulation path can be formed. The inlet and the outlet for the liquid may share the same opening by, for example, partitioning the flow path using an inner wall.

The heat sink 262 is one example of the second heat exchanger 22, and it conducts the thermal exchange between the liquid flowing through the heat sink 262 and the air around the heat sink 262. The heat sink 262 is disposed on the conduit 264 connecting the cold plate 261 and the pump 263. The heat sink 262 in this arrangement can absorb the heat from the warmed liquid and release the heat to the outside of the heat sink 262 so that the liquid is cooled and then used again for cooling the detector 12.

The heat sink 262 is a component including, for the liquid, an inlet, a flow path, fins, and an outlet. The fins constitute one example of the heat dissipation section of the second heat exchanger 22. The heat sink 262 may be formed of a material that gives a high thermal conduction efficiency, for example, one or more metal materials such as copper, aluminum, etc., as the thermal exchange between the fins contacting the air and the liquid flowing through the flow path is performed. The metal materials forming the heat sink 262 may have a high specific heat capacity so that the heat sink 262 can endure the thermal load applied during the rotation of the gantry unit 10.

The flow path in the heat sink 262 may be freely designed, utilizing any straight, curved, meandering profiles, etc., so that the warmed liquid can be cooled entirely and uniformly. The diameter, length, number, shape, etc. of the flow path may also be freely determined. Also, as long as the release of the warmed air is not hindered, the positions, orientations, number, shapes, etc. of the fins may be freely determined.

The pump 263 causes the liquid to circulate in the liquid-cooling unit 26. The pump 263 is disposed on the conduit 264 connecting the heat sink 262 and the cold plate 261. The pump 263 in this arrangement can supply the liquid cooled by the heat sink 262 to the cold plate 261.

Additionally, the pump 263 may also serve as a reservoir for temporarily holding the liquid. Power supply for the pump 263 may be done via a slip ring furnished on the rotary frame 13. The pump 263 may be controlled by the adjustment function 445.

The conduit 264, which may also be called a pipe, tube, hose, or the like, is one example of the connecting section and forms a circulation path through which the liquid flows. The conduit 264 may be formed of a hard material or a soft material. The conduit 264 may be, for example, cylindrical to conform to the shape of the inlet and outlet of each component. The conduit 264 may be freely designed to form the circulation path, utilizing any straight, curved, meandering profiles, etc.

Note that, according to the cooling amount required, multiple of the liquid-cooling units 26 may be provided, and the number of the components constituting each liquid-cooling unit 26 may be increased.

FIG. 3 uses arrows to indicate the flow of the liquid in the liquid-cooling unit 26 configured as described above. The liquid is fed from the pump 263 and enters the cold plate 261 via its inlet. The liquid absorbs heat from the detector 12 while flowing through the flow path. The warmed liquid comes out from the outlet of the cold plate 261 and is sent to the heat sink 262, where it releases the heat and returns to the cold liquid again. The cold liquid enters the pump 263 and repeats the circulation through the same route.

Figure 4:
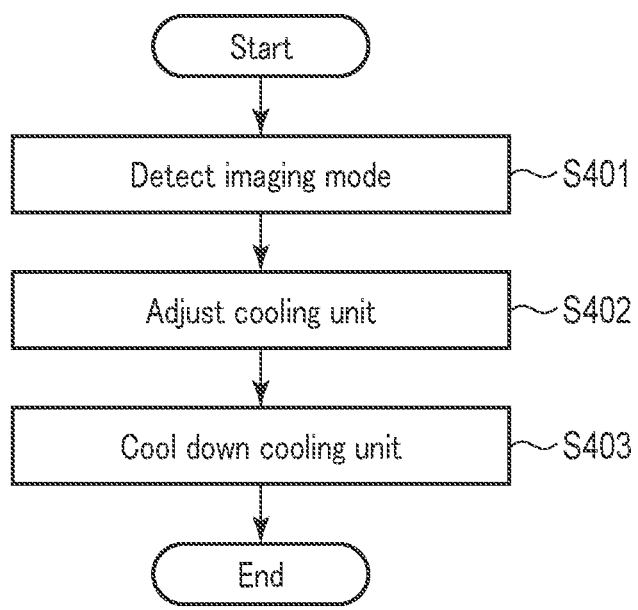
FIG. 4 is a flowchart for explaining an exemplary operation of the X-ray CT apparatus according to the embodiment.

Next, an exemplary operation of the X-ray CT apparatus 1 according to the embodiment will be described with reference to FIG. 4. Note that the operations performed by the X-ray CT apparatus include imaging-related operations as well, but the description here will concentrate on the operations related to the adjustment with the cooling unit 20.

In step S401, the detection function 444 detects the imaging mode. The imaging mode here is, for example, a mode set by an operator via the input interface 43 and stored in the memory 41. More specifically, the detection function 444 accesses the memory 41 to detect the imaging mode.

In step S402, the adjustment function 445 controls the cooling unit 20 according to the detected imaging mode. More specifically, the adjustment function 445 adjusts the output of the cooling unit 20, that is, the cooling amount, so that the temperature of the detector 12 is kept within the temperature range that allows the detector 12 to give its normal performance.

In adjusting the cooling amount, a method may be adopted in which, for example, a correlation between each imaging mode and the heat generation amounts of the detector 12 is measured and stored as a correlation table in the memory 41 in advance of the imaging operations. For a photon counting CT apparatus as one exemplary implementation, the correlation table showing heat generation amounts under each of the substance discrimination mode and the substance non-discrimination mode may be prepared in advance. For an X-ray CT apparatus that uses an energy integrating detector, a correlation table showing, for example, tube currents, tube voltages, and a heat generation amount corresponding to each instance of the tube currents and the tube voltages may be prepared in advance. Such correlation tables may be prepared during the manufacture of the X-ray CT apparatus 1, or during the maintenance of the detector 12.

The X-ray CT apparatus 1, with reference to the correlation table, predicts the change in the heat generation amount of the detector 12 that would occur upon the imaging mode switchover. Based on this prediction, the output of the cooling unit 20 is adjusted during the imaging operation. A correlation table showing each imaging mode and the heat generation amounts of the DAS 18 may also be prepared, together with the correlation table for the detector 12. In this case, the output of the cooling unit 20 may be adjusted so that the sum of the amount of heat generated by the detector 12 and the amount of heat generated by the DAS 18 will be canceled out.

Another method for adjusting the cooling amount is, for example, to provide a temperature measuring instrument, such as a thermistor, in the detector 12 so that the current temperature of the detector 12 is measured. The X-ray CT apparatus 1 may thus continuously monitor the current temperature of the detector 12 during the ongoing imaging operation to adjust the output of the cooling unit 20 for maintaining the detector 12 at a constant temperature.

In step S403, the processing circuitry 44 cools the cooling unit 20. For example, the processing circuitry 44 activates the fans disposed at the air inlet 23 and the air outlet 24 to cool the cooling unit 20. The cooling here may be performed to the degree that the cooling medium in the cooling unit 20 reaches a temperature that enables efficient cooling of the detector 12 again.

Figure 5:
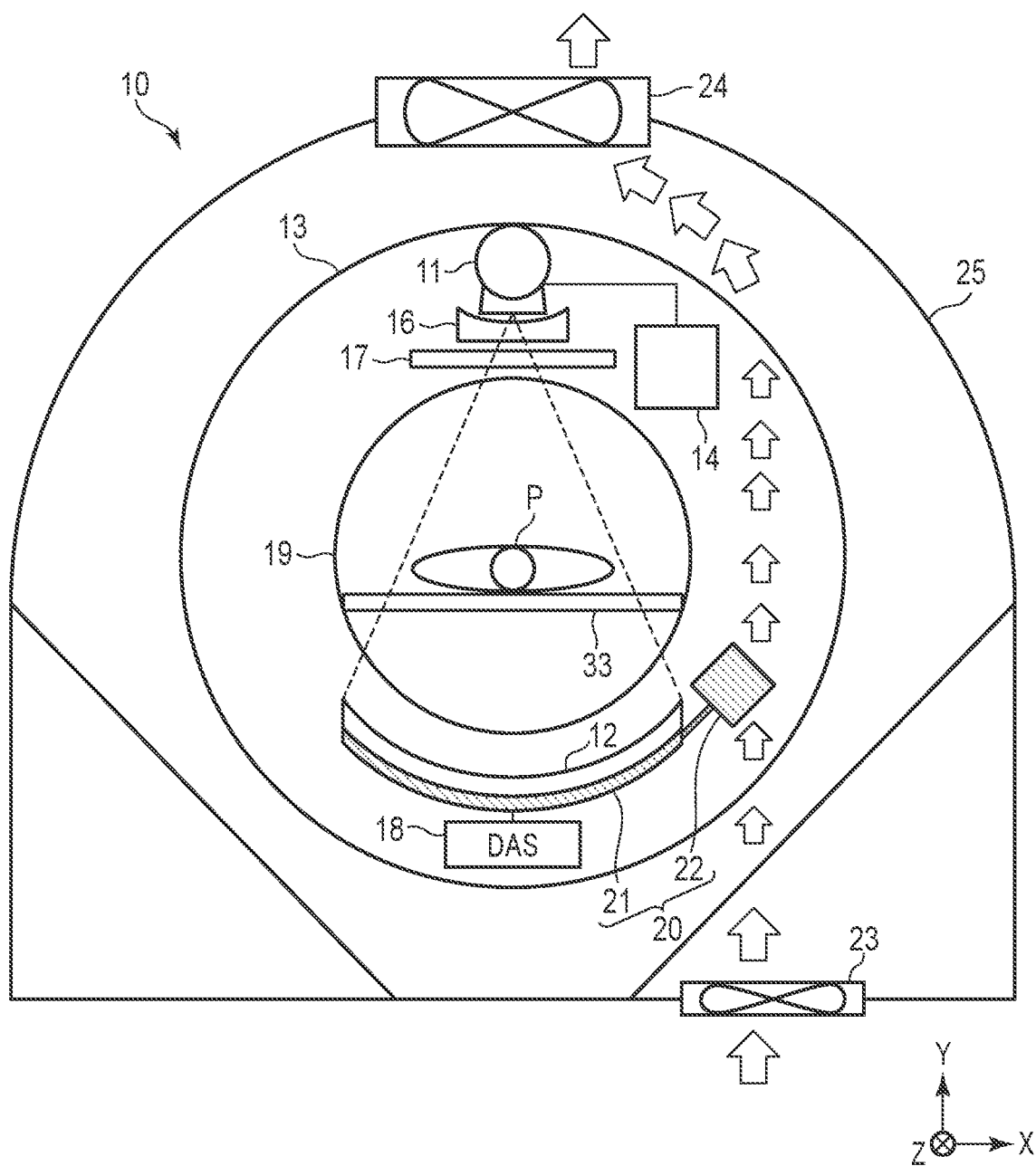
FIG. 5 is a diagram showing an example of a heat discharging path in the X-ray CT apparatus according to the embodiment.

FIG. 5 will be referred to for explaining an example of the heat discharging path in the X-ray CT apparatus 1 according to the embodiment. The heat discharging path shown here is for cooling the cooling unit 20 when the gantry unit 10 is in a stationary, non-rotating state. It will be assumed that the air inlet 23 and the air outlet 24 each open in the housing 25 such that air can be moved in or moved out of the rotary frame 13. The figure indicates the flow of air using arrows.

The cooling unit 20 cools the detector 12 in a continuous manner so that the detector 12, which generates heat during imaging operations, can suppress the temperature non-uniformity to a given extent. When the rotary frame 13 is stopped from rotating after an imaging operation, air is taken via the air inlet 23 located in the bottom face of the housing 25 in order to cool the cooling unit 20 that has been warmed. The intake air ascends and reaches the heat dissipation section of the second heat exchanger 22 where it cools the cooling medium. The air thus warmed by the heat dissipation section ascends, and is discharged to the outside of the gantry unit 10 via the air outlet 24 located in the top face of the housing 25. The circulation of air through the inside and outside of the gantry unit 10, which uses such a heat discharging path, continuously cools the cooling medium of the cooling unit 20 and makes it ready for the next imaging operation. Note that the cooling unit 20 may also cool the detector 12 during the period where the rotary frame 13 is stationary.

Next, a concrete example of the operation of the X-ray CT apparatus 1 according to the embodiment will be described with reference to FIGS. 6 and 7. The description will assume an exemplary instance where a photon counting detector is adopted as the detector 12. It will also be assumed that the heat from the DAS 18 is dominant over the detector 12, and the output of the cooling unit 20 is to be adjusted according to the change in the amount of heat generation by the DAS 18.

In the X-ray CT apparatus 1 with the detector 12 as a photon counting detector, the heat generation amount of the DAS 18 is influenced greatly by the difference between imaging modes, i.e., the substance discrimination mode and the substance non-discrimination mode. Thus, the temperature of the detector 12 is kept constant by adjusting the output of the cooling unit 20 in such a manner as to provide a cooling amount that can cancel out the variation in the heat generation amount of the DAS 18 due to the difference in imaging modes. More specifically, when the imaging mode is the substance discrimination mode, the adjustment function 445 adopts a cooling amount that is increased from the cooling amount adopted in the substance non-discrimination mode.

Figure 6:
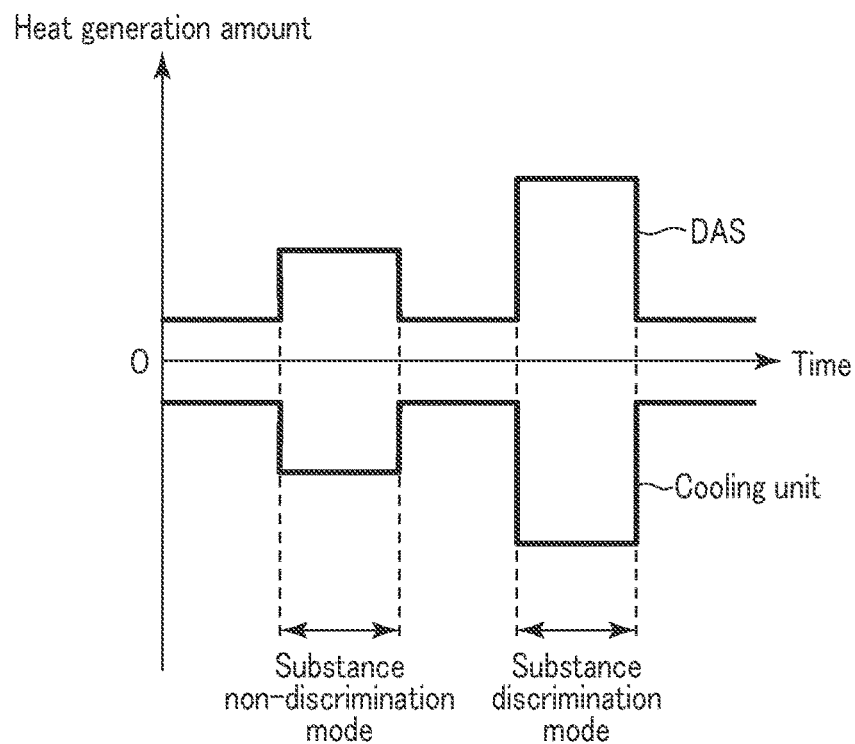
FIG. 6 is a diagram showing a concrete example of the operation of the X-ray CT apparatus according to the embodiment.

FIG. 6 is a graph showing the amount of heat (including positive and negative values) generated by each of the DAS 18 and the cooling unit 20, before and after the imaging mode switchover. In the graph, the horizontal axis indicates time and the vertical axis indicates the amount of heat generation, so the solid lines indicate the temporal changes in heat generation amount of the DAS 18 and the cooling unit 20, respectively. The DAS 18 requires more power in the substance discrimination mode than in the substance non-discrimination mode, and increases its heat generation amount in proportion to the power consumed. According to the graph, as such, the DAS 18 shows a higher heat generation amount in the substance discrimination mode.

Here, the adjustment function 445 adjusts the output of the cooling unit 20 so that the cooling unit 20 gives a cooling amount (negative heat generation amount) that cancels out the heat generation amount (positive heat generation amount) of the DAS 18. More specifically, the adjustment is performed in such a manner that the heat generation amount of the DAS 18 and the cooling amount of the cooling unit 20 are equal to each other at every point in time. Consequently, the graph depicts the profile for the cooling unit 20 as an inversion of the profile for the DAS 18 with respect to the horizontal axis.

Figure 7:
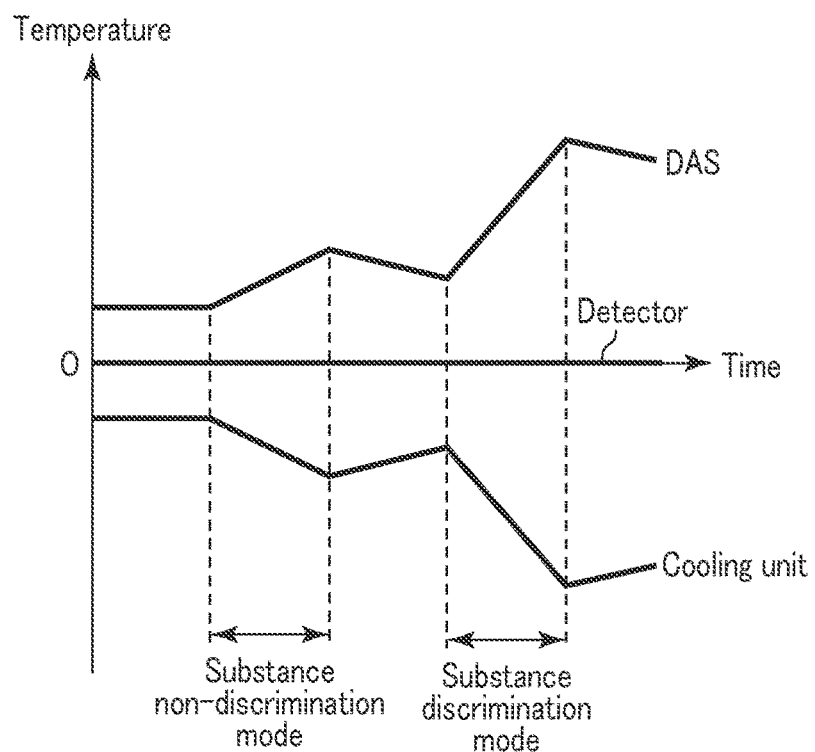
FIG. 7 is a diagram showing the concrete example of the operation of the X-ray CT apparatus according to the embodiment from another aspect.

FIG. 7 is a graph showing the temperature of each of the DAS 18, the cooling unit 20, and the detector 12 before and after the imaging mode switchover. In the graph, the horizontal axis indicates time and the vertical axis indicates a temperature, so the solid lines indicate the temporal changes in temperature of the DAS 18, the cooling unit 20, and the detector 12, respectively. When the heat generation amount of the DAS 18 and the cooling amount of the cooling unit 20 change as shown in FIG. 6, the heat generation amount of the DAS 18 is canceled out by the cooling amount of the cooling unit 20 at every point in time, and therefore, the detector 12 experiences no temperature change (temperature change amount=0). Accordingly, the temperature of the detector 12 is kept constant even upon occurrence of the imaging mode switchover.

While the temperature of the detector 12 can be kept constant by means of the adjustment function 445 adjusting the output of the cooling unit 20 in the above manner, the embodiment is not limited to this. As another exemplary implementation, the temperature of the detector 12 may be kept constant without the control of the control circuitry 44 by designing the circuit components so that the cooling unit 20 changes its output in proportion to the power consumption at the DAS 18.

Figure 8:
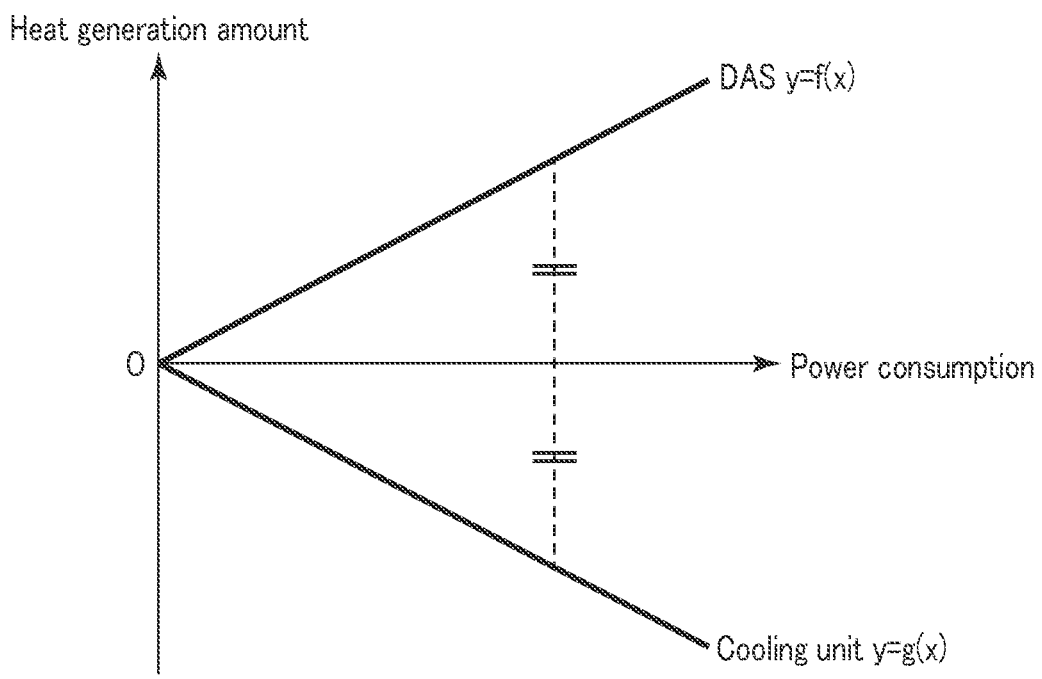
FIG. 8 is a diagram showing exemplary circuit control for the cooling unit according to the embodiment.
Figure 9:
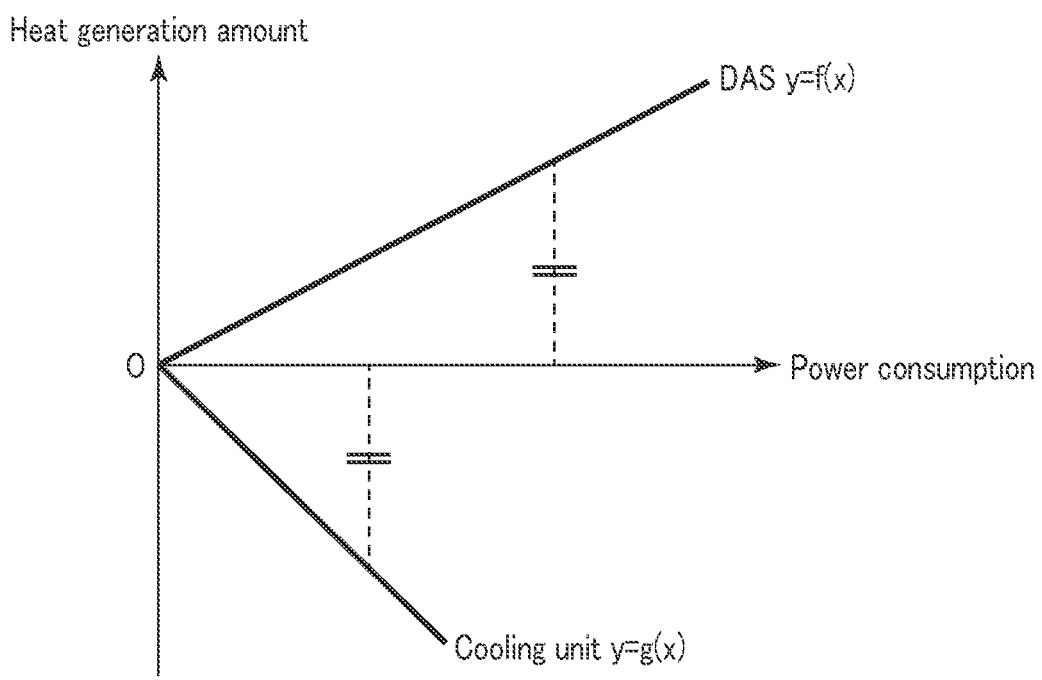
FIG. 9 is a diagram showing another exemplary circuit control for the cooling unit according to the embodiment.
Figure 10:
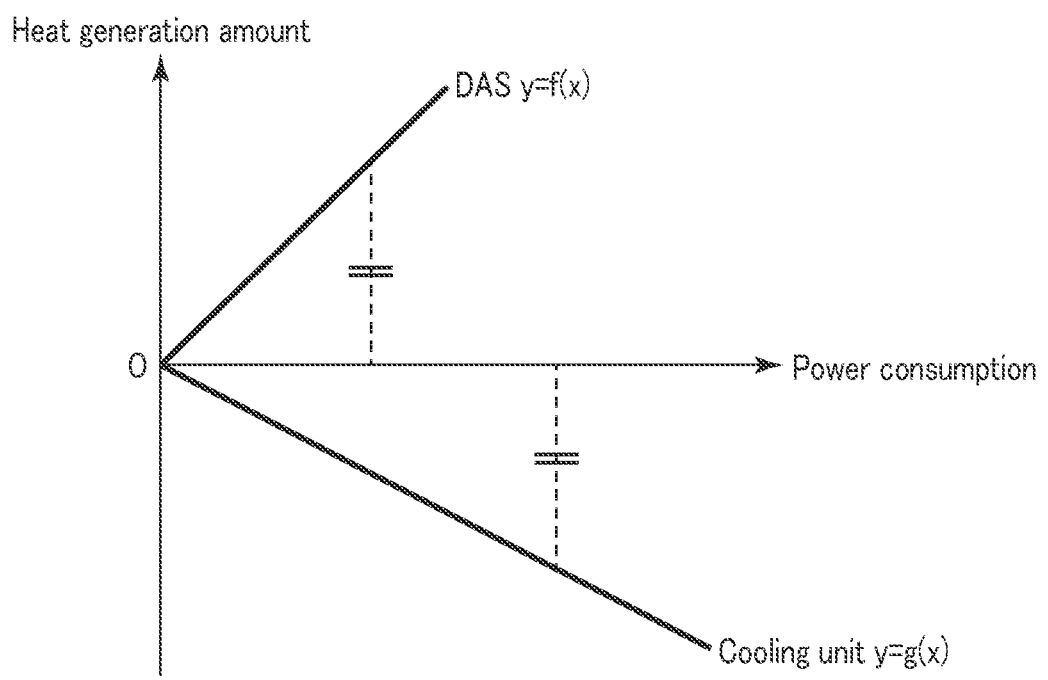
FIG. 10 is a diagram showing yet another exemplary circuit control for the cooling unit according to the embodiment.

Next, FIGS. 8, 9, and 10 will be referred to for explaining examples of circuit control for the cooling unit 20 according to the embodiment. It will be assumed that the control is performed according to the power consumption at each of the DAS 18 and the cooling unit 20.

In order to keep the temperature of the detector 12 constant, the heat generation amount of the DAS 18 and the cooling amount of the cooling unit 20 should be balanced with each other. The description will use a symbol "x" to indicate the power consumption of each of the DAS 18 and the cooling unit 20, and a symbol "y" to indicate the heat generation amount (cooling amount). Here, y is given as a function of x. For the DAS 18, the relationship between the power consumption x and the heat generation amount y is represented by $y=f(x)$. For the cooling unit 20, the relationship between the power consumption x and the cooling amount y is represented by $y=g(x)$. As the heat generation amount (cooling amount) of the DAS 18 and the cooling unit 20 is proportional to the respective power consumption x, the graphs in the figures depict a profile for the DAS 18 that is a straight line extending from the origin O and rising to the right, and a profile for the cooling unit 20 that is a straight line extending from the origin O and falling to the right.

FIG. 8 assumes a case where the heat generation amount produced by the DAS 18 and the cooling amount produced by the cooling unit 20 at the same power consumption match each other (relational expression: $f(x)=-g(x)$). In this case, for example, connecting the DAS 18 and the cooling unit 20 using a parallel circuitry configuration makes values of the current and the voltage to one of the DAS 18 and the cooling unit 20 always conform to values of the current and the voltage to the other. Accordingly, even when a current flowing into the entire parallel circuitry and the voltage applied thereto are varied, the heat generation amount of the DAS 18 can be canceled out by the cooling amount of the cooling unit 20 (relational expression: [DAS 18's heat generation amount]+[cooling unit 20's cooling amount]=0), since the power consumption at the DAS 18 and the power consumption at the cooling unit 20 are always the same as each other.

FIG. 9 assumes a case where the heat generation amount produced by the DAS 18 is smaller than the cooling amount produced by the cooling unit 20 at the same power consumption (relational expression: $f(x)<-g(x)$, $x\neq 0$). In other words, this is a case where the cooling unit 20 provides a cooling rate higher than the heat generation rate of the DAS 18. Here, the circuit design, the resistance value for the cooling unit 20, etc. may be modified so that the power consumption at the cooling unit 20 is adjusted. For example, for the connection of the DAS 18 and the cooling unit 20 in a serial circuitry configuration, the circuitry may be designed so that the resistance value for the cooling unit 20 is smaller than the resistance value for the DAS 18. For the connection of the DAS 18 and the cooling unit 20 in a parallel circuitry configuration, the circuitry may be designed so that the resistance value for the cooling unit 20 is larger than the resistance value for the DAS 18. In the above manner, it is possible to align the heat generation amount of the DAS 18 and the cooling amount of the cooling unit 20 with each other by making the power consumption at the cooling unit 20 smaller than the power consumption at the DAS 18.

FIG. 10 assumes a case where the heat generation amount produced by the DAS 18 is larger than the cooling amount produced by the cooling unit 20 at the same power consumption (relational expression: $f(x)>-g(x)$, $x\neq 0$). In other words, this is a case where the cooling unit 20 provides a cooling rate lower than the heat generation rate of the DAS 18. Also in this case, the circuit design, the resistance value for the cooling unit 20, etc. may be modified so that the power consumption at the cooling unit 20 is adjusted. For example, for the connection of the DAS 18 and the cooling unit 20 in a serial circuitry configuration, the circuitry may be designed so that the resistance value for the cooling unit 20 is larger than the resistance value for the DAS 18. For the connection of the DAS 18 and the cooling unit 20 in a parallel circuitry configuration, the circuitry may be designed so that the resistance value for the cooling unit 20 is smaller than the resistance value for the DAS 18. In the above manner, it is possible to align the heat generation amount of the DAS 18 and the cooling amount of the cooling unit 20 with each other by making the power consumption at the cooling unit 20 larger than the power consumption at the DAS 18.

The configurations and operations of the X-ray CT apparatus according to the embodiment have been described, but no limitations have been intended. For example, the means for cooling the detector 12 is not limited to the cooling unit 26 shown in FIG. 3, but may be an air-cooling unit or an electron-cooling unit.

As one exemplary implementation with an air-cooling unit, the X-ray CT apparatus 1 includes at least one fan. The adjustment function 445 may cool the detector 12 by adjusting at least one of the rotating speed, the number of times of driving, and/or the position of driving of such a fan or fans arranged to cool the detector 12. As one exemplary implementation with an electron-cooling unit, the X-ray CT apparatus 1 includes at least one Peltier device. The adjustment function 445 may cool the detector 12 by adjusting at least one of the current value, the number of times of driving, and/or the position of driving of such a Peltier device or devices arranged to cool the detector 12.

Also, the output of the cooling unit 20 may be adjusted according to the bin number used for imaging operations. Typically, use of a larger bin number in the substance discrimination mode is accompanied by a measurement based on X-ray photon energy in the units of finer energy bands, and allows the detector 12 to collect a larger amount of data. The DAS 18, in order to process an increased amount of data, uses more calculation circuits and generates more heat. That is, the bin number and the heat generation amount of the DAS 18 are proportional to each other, and it is therefore possible to adjust the cooling amount of the cooling unit 20 according to the bin number, by predicting the heat generation amount of the DAS 18 from the bin number for use in the imaging mode. As one concrete example, when the imaging mode is a mode for collecting data with a first bin number, the adjustment function 445 may adopt a cooling amount that is increased from the cooling amount adopted in a mode for collecting data with a second bin number smaller than the first bin number.

Moreover, the cooling amount of the cooling unit 20 may also be adjusted based on at least one of the values of the tube current and/or the tube voltage of the X-ray tube 11, in addition to or instead of based on the imaging mode, i.e., the difference between the substance non-discrimination mode and the substance discrimination mode. Generally, values of the tube current and the tube voltage of the X-ray tube 11 and the heat generation amount of the DAS 18 are proportional to each other, and it is therefore possible to adjust the cooling amount of the cooling unit 20 according to the values of the tube current and/or the tube voltage of the X-ray tube 11, by predicting the heat generation amount of the DAS 18 from the values of the tube current and/or the tube voltage of the X-ray tube 11.

Additionally, use of a heater together with the cooling unit 20 is also possible in order for the adjustment to keep the temperature of the detector 12 constant. For example, when the cooling unit 20 is the liquid-cooling unit 26, a heater may be provided in the liquid-cooling unit 26 so that the liquid flowing through the flow path is warmed by the heater and increases its temperature. This enables the liquid-cooling unit 26 to also operate as a heating unit, and the temperature of the detector 12 can be kept constant even when the target temperature is high.

Note that the cooling unit 20 and the heater may be separate from each other. In one implementation, the heater may be disposed at a position where it can warm up the detector 12 while not interfering with the cooling unit 20. The heater may be controlled in a similar manner to the control of the cooling unit 20 for adjusting its heating amount.

The detector 12 according to the embodiment may be either an energy integrating detector or a photon counting detector. When the detector 12 according to the embodiment is an energy integrating detector, the substance discrimination mode may be realized by utilizing multiple scanning operations with different tube voltages, such as operations with a dual-energy CT.

According to at least one embodiment described above, the heat generation amount of a detector is predicted from the imaging mode, and the temperature adjustment amount such as a cooling amount or a heating amount is adjusted according to the imaging mode, so that when, for example, cooling of the detector is intended, the detector can be efficiently cooled. Here, measuring the actual temperature of the detector also allows for the real-time cooling of the detector. Consequently, the temperature non-uniformity in the detector can be suppressed even in the event of imaging mode changes, and providing high-resolution images is ensured.

While certain embodiments have been described, they have been presented by way of example only, and are not intended to limit the scope of the inventions. Indeed, the novel embodiments described herein may be embodied in a variety of other forms. Furthermore, various omissions, substitutions, and changes in the form of the embodiments may be made without departing from the spirit of the inventions. The accompanying claims and their equivalents are intended to cover such forms or modifications as would fall within the scope and spirit of the inventions.

The invention claimed is:

1. An X-ray computed tomography apparatus, comprising:
   an X-ray tube configured to radiate X-rays;
   a photon counting detector configured to detect the X-rays radiated from the X-ray tube and transmitted through a subject; and
   processing circuitry configured to adjust a temperature adjustment amount used to regulate a temperature of the photon counting detector according to whether an imaging mode is a substance discrimination mode or a substance non-discrimination mode.

2. The X-ray computed tomography apparatus according to claim 1, wherein
   the temperature adjustment amount is a cooling amount to cool the photon counting detector, and
   the processing circuitry is further configured to adjust the cooling amount so that a first cooling amount when the imaging mode is a substance discrimination mode, is larger than a second cooling amount when the imaging mode is a substance non-discrimination mode.

3. The X-ray computed tomography apparatus according to claim 2, further comprising at least one of cooling units, comprising a liquid-cooling unit, an air-cooling unit, and an electron-cooling unit,
   wherein the processing circuitry is further configured to adjust the cooling amount by controlling the at least one of the cooling units.

4. The X-ray computed tomography apparatus according to claim 3, wherein the at least one of cooling units comprises
   a first heat exchanger extending in a channel direction of the photon counting detector and in thermal contact with the photon counting detector, and
   a second heat exchanger disposed on a side of at least one lateral end of the photon counting detector.

5. The X-ray computed tomography apparatus according to claim 4, further comprising:
   a rotary member to which the X-ray tube, the photon counting detector, and the at least one of cooling units are attached, and a housing comprising, at a position near the second heat exchanger when the rotary member is in a non-rotating state, at least one air inlet to supply air to a heat dissipation section of the second heat exchanger.

6. The X-ray computed tomography apparatus according to claim 3, wherein
the at least one of the cooling units comprises at least one fan to cool the photon counting detector, and
the processing circuitry is further configured to adjust at least one of a rotating speed, a number of times of driving, and a position of driving of the fan.

7. The X-ray computed tomography apparatus according to claim 5, wherein
the at least one of the cooling units comprises at least one Peltier device for cooling the photon counting detector, and
the processing circuitry is further configured to adjust at least one of a current value, a number of times of driving, and a position of driving of the Peltier device.

8. The X-ray computed tomography apparatus according to claim 3, further comprising a data acquisition system configured to acquire imaging data from the photon counting detector,
wherein the processing circuitry is further configured to adjust a power consumption at the at least one of the cooling units according to a power consumption at the data acquisition system.

9. The X-ray computed tomography apparatus according to claim 1, wherein
the temperature adjustment amount is a cooling amount to cool the photon counting detector, and
the processing circuitry is further configured to adjust the cooling amount so that a first cooling amount when the imaging mode is a first mode for collecting data with a first bin number, is larger than a second cooling amount when the imaging mode is a second mode for collecting data with a second bin number, the first bin number being larger than the second bin number.

10. The X-ray computed tomography apparatus according to claim 1, wherein
the temperature adjustment amount is a cooling amount to cool the photon counting detector, and
the processing circuitry is further configured to adjust the cooling amount according to at least one of values of a tube current and a tube voltage of the X-ray tube.

11. The X-ray computed tomography apparatus according to claim 1, wherein the processing circuitry is further configured to change the temperature adjustment amount over time while imaging data is being collected.

12. The X-ray computed tomography apparatus of claim 1, the substance discrimination mode of the X-ray CT apparatus is a mode in which a substance discrimination process is performed.

13. An X-ray computed tomography apparatus, comprising:
an X-ray tube configured to radiate X-rays;
a photon counting detector configured to detect the X-rays radiated from the X-ray tube and transmitted through a subject; and
processing circuitry configured to adjust a cooling amount to reduce a temperature of the photon counting detector according to whether imaging data is collected using one bin or a plurality of bins.

14. The X-ray computed tomography apparatus according to claim 13, wherein the processing circuitry is further configured to change the cooling amount over time while the imaging data is being collected.

15. A method for adjusting a temperature of a photon counting detector configured to detect X-rays radiated from an X-ray tube and transmitted through a subject, the method comprising:
adjusting a cooling amount to reduce a temperature of the photon counting detector according to whether imaging data is collected using one bin or a plurality of bins.

* * * * *